US006833363B2

(12) United States Patent
Renier et al.

(10) Patent No.: US 6,833,363 B2
(45) Date of Patent: Dec. 21, 2004

(54) N-SULPHATED HYALURONIC ACID COMPOUNDS, DERIVATIVES THEREOF AND A PROCESS FOR THEIR PREPARATION

(75) Inventors: David Renier, Mestrino Padue (IT); Lanfranco Callegaro, Thiene Vicenza (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 09/972,707

(22) Filed: Oct. 3, 2001

(65) Prior Publication Data

US 2002/0037874 A1 Mar. 28, 2002

Related U.S. Application Data

(62) Division of application No. 09/402,510, filed as application No. PCT/EP98/01973 on Apr. 3, 1998, now abandoned.

(30) Foreign Application Priority Data

Apr. 4, 1997 (IT) ........................................ PD97A0064
Feb. 10, 1998 (IT) ........................................ PD98A0022

(51) Int. Cl.[7] .............................................. A61K 31/728
(52) U.S. Cl. .......................................... 514/54; 536/53
(58) Field of Search .............................. 514/54; 536/53

(56) References Cited

U.S. PATENT DOCUMENTS

| | | | | |
|---|---|---|---|---|
| 4,736,024 A | * | 4/1988 | Della Valle et al. | 536/55.3 |
| 4,784,991 A | * | 11/1988 | Nimrod et al. | 514/62 |
| 5,644,049 A | * | 7/1997 | Giusti et al. | 536/53 |
| 5,658,582 A | * | 8/1997 | Dorigatti et al. | 424/402 |
| 5,676,964 A | * | 10/1997 | Della Valle et al. | 424/423 |
| 5,763,504 A | * | 6/1998 | Matsuda et al. | 522/87 |
| 5,879,359 A | * | 3/1999 | Dorigatti et al. | 606/152 |
| 6,017,901 A | * | 1/2000 | Khan et al. | 514/54 |
| 6,027,741 A | * | 2/2000 | Cialdi et al. | 424/422 |
| 6,458,774 B1 | * | 10/2002 | Burger et al. | 514/54 |

FOREIGN PATENT DOCUMENTS

| | | |
|---|---|---|
| EP | 0265116 A2 * | 4/1988 |
| EP | 0340628 A2 | 8/1989 |
| EP | 0464759 A2 | 8/1992 |
| WO | WO 952571 | 9/1995 |

OTHER PUBLICATIONS

Magnani, A. et al.; "Blodd–Interation Performance of Differently Sulphated Hyaluronic Acids"; Thrombosis Research, vol. 81, No. 3, 1996, pp. 383–395.

* cited by examiner

Primary Examiner—Sameuel Barts
Assistant Examiner—Leigh C. Maier
(74) Attorney, Agent, or Firm—Birch, Stewart, Kolasch & Birch, LLP

(57) ABSTRACT

The present invention is directed to novel sulphated compounds of hyaluronic acid and derivatives thereof, optionally salified, wherein the glucosamines are partially N-sulphated and partially or totally O-sulphated in position 6. The compounds of the invention have anticoagulant and antithrombotic activities and are useful in the preparation of pharmaceutical compositions and biomaterial and in the production of coatings for biomaterials compositions and biomaterials and in the production of coating for biomedical objects.

26 Claims, No Drawings

N-SULPHATED HYALURONIC ACID COMPOUNDS, DERIVATIVES THEREOF AND A PROCESS FOR THEIR PREPARATION

This application is a divisional of application Ser. No. 09/402,510, filed on Dec. 6, 1999, now abandoned for which priority is claimed under 35 U.S.C. §120. Application Ser. No. 09/402,510 is the national phase of PCT International Application No. PCT/EP98/01973 filed on Apr. 3, 1998 under 35 U.S.C. §371. The entire contents of each of the above-identified applications are hereby incorporated by reference. This application also claims priority of Application No. PD97A000064 and PD98A000022 filed in Italy on Apr. 4, 1997 and Feb. 10, 1998 under 35 U.S.C. §119.

FIELD OF THE INVENTION

The present invention concerns new sulphated compounds of hyaluronic acid and derivatives thereof having anticoagulant and antithrombotic activities and processes for their preparation. Said compounds are useful in the preparation of pharmaceutical compositions and biomaterials and in the production of coatings for biomedical objects.

BACKGROUND OF THE INVENTION

Heparin is the sulphated glycosaminoglycan with the greatest biological activity. Its antithrombotic and anticoagulant properties are well known. Indeed, it is used in treatment for cardiovascular pathologies where there is a risk of thrombosis, and it has contributed notably to the successful outcome of open-heart surgery. The structure of heparin is not altogether known.

Commercial heparin comprises a range of 21 different kinds (Nader et al., 1974, Biochem. Biophys. Res. Commun. 57:488), with a molecular weight of between 3,000 and 37,500 Da, and with varying anticoagulant activity.

Heparin's anticoagulant activity depends on its structural characteristics, for example, on the degree of sulphation, on the degree of dissociation, on the sequence of the COO— and $SO_3$— groups, on the shape and size of the molecule. These factors are important to the formation of the ion bonds responsible for heparin's biological activity (Stivala et al., 1967, Arch. Biochem. Biophys. 122:40).

Because of the high density of its negative charge, heparin has a strong affinity for cations and its activity is pH-dependent. In particular, the N-sulphated group of its glucosamine residue plays a fundamental role in the interaction with the factors regulating the coagulative processes.

A significant reduction in the N-sulphated groups drastically reduces its anticoagulant and antithrombotic activities.

Many natural polysaccharides have been sulphated in order to obtain heparin-like products (Hoffman et al., 1982, Carbohydrate Res. 2:115; Kindness et al., 1980, Brit. J. Pharmac. 69:675; Horton et al., 1973, Carbohydrate Res. 30:349; Okada et al., 1979, Makromol. Chem. 180:813; Kikuchi et al., 1979, Nippon Kagaku Kaishi 1:127; Manzac et al., 1981, Proc. Third M.I.S.A.O. 5:504). Moreover, sulphuric, carboxy or sulphonated groups have been attached to synthetic polymers such as polystyrene (Kanmaugue et al., 1985, Biomaterials, 6:297) and polyurethanes (Ito et al., 1992, Biomaterials, 13:131).

However, the anticoagulant activity of these materials is much lower than that of heparin and depends on the type of substituent, the type of bond, the degree of substitution and the sequence.

Lastly, some chemical reactions for the sulphation of polysaccharides are known (WO 88/00211; EP 0340628; Carbohydrate Research, 158, 183–190, 1986) but no derivatives have ever been obtained which present, besides the chemical-physical characteristics peculiar to polysaccharides, any new characteristics such as anticoagulant activity.

In the international patent application, Publication No. WO 95/25751, a process is described for the non-selective sulphation of hyaluronic acid and the derivatives thereof to obtain compounds with an antithrombotic activity.

Their ability to inactivate thrombin is due to the formation of electrostatic interactions depending on the charge density, which increases according to the degree of sulphation, while heparin's activity is the consequence of a direct interaction with antithrombin III (T. W. Barrowcliffe et al., Journal of Pharmaceutical & Biomedical Analysis, Vol. 7, No. 2, pages 217–226, 1989; Peter D. J. Grootenhuiis et al., J. Am. Chem. Soc., 113, 2743–2747, 1991).

Heparin is widely used, although it does present side effects such as haemorrhagic effects, which prevent its being used too freely or without medical guidance.

Moreover, because of its chemical-physical characteristics, heparin cannot be used as a biomaterial but simply as a coating for other materials, and in sufficiently small quantities to avoid its causing localized bleeding.

Lastly, by acting directly on the coagulation factors, the anticoagulant action of heparin begins very rapidly and its duration, albeit dose-dependent, is generally similarly brief. These drawbacks limit its applicability in certain surgical fields such as cardiovascular surgery involving the implantation of devices requiring an absolute absence of thrombogenicity for a given length of time.

SUMMARY OF THE INVENTION

The present invention is directed to novel sulphated compounds of hyaluronic acid and the derivatives thereof, optionally salified, with an anticoagulant and antithrombotic activity, wherein the glucosamines are partially N-sulphated or partially N-sulphated and partially or totally O-sulphated in position 6, for the preparation of pharmaceutical formulations, biocompatible and bioabsorbable biomaterials with an anticoagulant activity and for the coating of biomedical objects and processes for their preparation.

The present invention also provides for a chemical process using a well-characterized starting product such as hyaluronic acid, which process allows for the selective sulphation of the amino group of glucosamine or the hydroxy group in the position 6, to thus obtain new sulphated derivatives of hyaluronic acid with an unaltered range of molecular weights and with an anticoagulant activity similar to that of heparin.

While the ability of hypersulphated polysaccharides to inactivate thrombin is due to the formation of electrostatic interactions depending on the charge density, which increases according to the degree of sulphation, the N-sulphated derivatives provided in the present invention appear to act on the coagulation factors by means of a specific an mechanism similar to that of heparin.

Further advantages of the present invention are represented by the improved chemical-physical characteristics of the N-sulphated derivatives compared to those of the hypersulphated derivatives, making them suitable for the preparation of biomaterials for use in the fields of biomedicine and health care and in the pharmaceutical field.

Moreover, the possibility of obtaining a compound with an anticoagulant and non-thrombogenic activity by means of selective sulphation of just the amino groups and hydroxy groups in position 6, notably reduces the costs of the process compared to the preparation of hyaluronic acid with all the hydroxy groups homogeneously sulphated.

DETAILED DESCRIPTION OF THE INVENTION

The term "partially 2-N-sulphated derivative" of hyaluronic acid as used herein means a product obtained by means of a controlled sulphation reaction of the amino group of the glucosamine of hyaluronic acid, previously N-deacetylated according to the procedure described by P. Shaklee (1984) Biochem. J. 217, 187–197. The reaction proceeds as illustrated below:

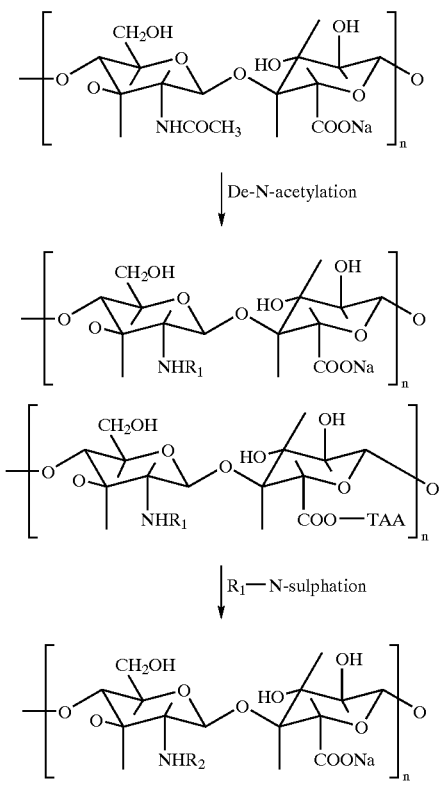

n: from 12 to 12500
$R_1$ = H, $COCH_3$
TAA = tetra-alkylammonium
$R_2$ = $SO_3$, $COCH_3$ The term "partially 2-N-sulphated and 6-O-sulphated derivatives" as used herein means the products of the chemical reaction illustrated in diagram 1, wherein, besides the amino group of glucosamine, the primary hydroxy function of the same residue is also totally or partially involved in the sulphation reaction, as illustrated below:

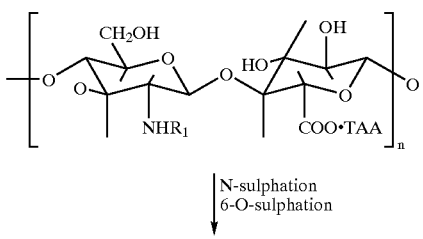

n: from 12 to 12500
$R_1$ = H, $COCH_3$
TAA = tetra-alkylammonium
$R_2$ = $SO_3$, $COCH_3$ The derivatives generated according to diagrams 1 and 2 can be used as intermediate reactants in the preparation of compounds, according to the procedure described in European patent 0216453 B1, wherein the carboxy function of the glucuronic residue of hyaluronic acid, partially 2-N-sulphated or partially 2-N-sulphated and partially or totally 6-O-sulphated, is partially or completely reacted with alcohols of the aliphatic, aromatic, arylaliphatic, cycloaliphatic, heterocyclic series, producing the respective partial or total esters:

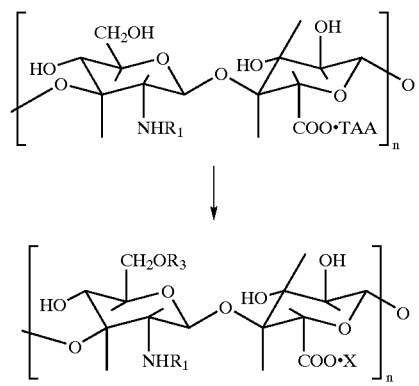

n: from 12 to 12500
$R_1$ = H, $COCH_3$
TAA = tetra-alkylammonium
$R_2$ = $SO_3$, $COCH_3$
$R_3$ = $SO_3$, H
X = alcoholic residue, Sodium Moreover, it is possible to use the synthetic derivatives according to diagrams 1 and 2 as intermediates in the preparation of crosslinked compounds, according to the procedures described in European patents 0341745 B1 and 265116 B1 respectively, wherein a part or all of the carboxy groups belonging to the D-glucuronic residue are reacted: i) using condensing agents with the alcohol functions of the same polysaccharide chain or other chains, generating inner (or lactone) esters and intermolecular esters; ii) with poly-alcohols of the aliphatic, aromatic, arylaliphatic, cycloaliphatic, heterocyclic series, generating crosslinking by means of spacer chains.

The above-said sulphated compounds obtained according to the process of the present invention can be optionally salified with heavy metals, the heavy metals being selected from the group of metal elements in the 4th, 5th and 6th periods of the periodical table, such as silver, iron, cobalt, copper, zinc, arsenic, strontium, zirconium, antimonium, gold, cesium, tungsten, selenium, platinum, ruthenium, bismuth, tin, titanium, and mercury. These salts can be used in dermatology, ophthalmology, dentistry, stomatology, rheumatology, urology, gynecology, internal surgery, as food supplements and as anti-oxidant, antirheumatic, antitumoral, antiinflammatory, analgesic and anti-ulcer agents.

Lastly, the sulphated derivatives can be optionally salified with pharmacologically active substances such as antibiotics, antiinfective, antimicrobial, antiviral, cytostatic, antitumoral, antiinflammatory and wound healing agents, anesthetics, cholinergic or adrenergic agonists or antagonists, antithrombotic, anticoagulant, haemostatic, fibrinolytic and thrombolytic agents, proteins and their fragments, peptides, and polynucleotides.

Apart from their above noted antithrombotic and anticoagulant properties and their biocompatibility characteristics, the N-sulphated derivatives of the present invention can be used advantageously as antiviral agents, for example against human immune deficiency virus (HIV) and herpes, and as anti-inflammatories for systemic, topical or local use, for example by the rectal or vaginal routes both in the form of pharmaceutical compositions and in the form of biomaterials.

The present inventive compounds and their salts can therefore be used advantageously, either alone or in association with one another or with other pharmacologically active substances, in combination with a pharmaceutically acceptable carrier for the preparation of pharmaceutical compositions.

Such pharmaceutical compositions can be used, for example, as antithrombotic, anticoagulant, antiinflammatory, antiviral, anti-oedematous preparations, to accelerate wound healing, in the treatment of burns, sores, skin ulcers, dental decay, restenosis and infarction and to favor angiogenesis.

Of special interest are formulations and biomaterials for the transport and release of biologically active substances such as proteins and their fragments, peptides, polynucleotides, growth factors, enzymes, vaccines, substances used in the treatment of diseases associated with genetic defects such as those depending on enzymatic hypo- or hyperactivity due to defects of the gene encoding for a given enzyme, deforming diseases and hereditary disorders.

The sulphated derivatives according to the present invention can be associated with radioactive and non-radioactive substances used in contrast systems, and used as tracers in in vivo diagnostics in the identification and cure of tumoral or damaged tissues.

One considerable advantage is represented by the possibility of processing the sulphated compounds and their salts in various forms of biomaterials such as sponges, films, membranes, threads, tampons, nonwoven fabrics, microspheres, nanospheres, gauzes, gels, guide channels. These biomaterials, in one such form or several forms together, can be constituted by one or more sulphated derivatives and by their salts, optionally included in association with other natural, synthetic, semisynthetic polymers and, optionally, with biologically active substances.

Examples of the natural polymers which can be used are collagen, coprecipitates of collagen and glycosaminoglycans, cellulose, polysaccharides in the form of gels such as chitin, chitosan, pectin or pectic acid, agar, agarose, xanthan, gellan, alginic acid or alginates, polymannan or polyglycans, starch, natural gums. The semisynthetic polymers for example can be chosen from the group consisting of crosslinked collagen with agents such as aldehydes or precursors of the same, dicarboxylic acids or their halogenides, diamines, derivatives of cellulose, hyaluronic acid, chitin or chitosan, gellan, xanthan, pectin or pectic acid, polyglycans, polymannan, agar, agarose, natural gum and glycosaminoglycans. Lastly, examples of synthetic polymers that can be used are polylactic acid, polyglycolic acid or copolymers of the same or their derivatives, polydioxanes, polyphosphazenes, polysulphonic resins, polyurethanes, PTFE.

The biomaterials thus obtained can be used in the cardiovascular field or in all applications involving contact with the blood or with highly vascularized body tissues where the biomaterial used needs to be totally free of thrombogenicity, besides having characteristics of biocompatibility and biodegradability due to the use of the ester derivatives of hyaluronic acid.

The above noted biomaterials can be used to advantage in various fields of surgery: in internal surgery, osteoarticular surgery, surgery to Hi the nerves, anastomosis, viscoelastic, ophthalmic, oncological, plastic, otorhinolaryngological, abdominal-pelvic, urogynaecological and cardiovascular surgery, such as in the preparation of cardiac valves, vascular stents, in the prevention of post-surgical adhesions, in the prevention of hypertrophic scarring.

Moreover, the sulphated compounds associated with fibrin, and possibly with other biologically active substances, can be used for the preparation of surgical glues.

The biomaterials according to the present invention can be used in other fields besides the surgical field, for instance in haemodialysis, cardiology, dermatology, ophthalmology, otorhinolaryngology, dentistry, gynaecology, urology, in extracorporeal blood circulation and oxygenation and in cosmetics.

The above noted biomaterials in their various forms can also be used to advantage as supports for cell cultures such as mesenchymal cells or mature cells to obtain connective tissue, glandular tissue and nerve tissue.

The instant biopolymers can also be used in processes to coat objects used both in the medical field and in other industrial sectors, to thereby give new biological characteristics to the surfaces of materials used as supports.

Examples of objects which can be thus coated are catheters, guide channels, probes, cardiac valves, soft tissue replacements, replacements of an animal origin such as cardiac valves from pigs, artificial tendons, bone and cardiovascular replacements, contact lenses, blood oxygenators, artificial kidneys, hearts, pancreas and liver, blood bags, syringes, surgical instruments, filtration systems, laboratory instruments, culture containers and containers for the regeneration of cells and tissues, supports for peptides, proteins, antibodies.

One method of coating the surfaces of these objects is the Plasma Coating technique described in international patent application No. WO96/24392, and illustrated in more detail hereafter in a preparation example. The process for the preparation of the compounds of the present invention mainly consists of two steps, the first involving the controlled N-deacetylation of the natural polysaccharide, and the second involving the specific sulphation reaction of the primary hydroxy or free amino functions of glucosamine.

Fractions of hyaluronic acid from biological and fermentation sources, with a molecular weight of between 5,000 and 5,000,000 Da, preferably between 50,000 Da and 300,000 Da, are solubilized in hydrazine hydroxide with a purity of no less than 98%, in a concentration range of between 1 and 50 mg/ml, preferably between 5 and 25 mg/ml. This solution is then supplemented with hydrazine sulphate in a weight/volume concentration varying between 0.1 and 3%, preferably 1%.

The reaction is conducted within a temperature range of 40 to 90° C., preferably 60° C., under agitation, for as long as it takes to reach the desired degree of N-deacetylation.

Table 1 hereafter reports the yield expressed as the percentage of free amino groups, in terms of time expressed as hours of reaction:

TABLE 1

| Test | Temperature | Time (hours) | N-deacetylation (%)* |
|---|---|---|---|
| DAc 1** | 60° | 4 | 3 |
| DAc 2 | 60° | 8 | 5 |
| DAc 3 | 60° | 16 | 9 |
| DAc 4 | 60° | 24 | 14 |
| DAc 5 | 60° | 48 | 23 |
| DAc 6 | 60° | 72 | 36 |

*The percentage of N-deacetylation is determined according to the method of J. Riesenfeld (Analy. Bioch. 1990, vol. 188, pages 383–389).
**"DAc" = N-deacetylation The reaction is then stopped by precipitation with a polar solvent, preferably ethanol. The precipitate is partially vacuum-dried and treated with a solution of iodic acid with a molarity range of between 0.1 and 1M, preferably 0.5M, and lastly, with iodohydric acid at a concentration of 57% (w/v). The pH of the solution is maintained between 5 and 7 by adding a solution of sodium acetate (10% w/v).

The aqueous phase containing the modified polysaccharide is extracted by repeated treatments with diethylether and then, once the yellow color has completely disappeared, the solution is treated again with ethanol.

The precipitate which forms, after further drying at 40° C., is solubilized in water at a concentration of between 10 ng/ml and 40 ng/ml, preferably 25 ng/ml, and the solution is percolated through a column containing an ion exchange resin activated with a tetraalkylammonium hydroxide, where the alkyl residue of the quaternary ammonium is constituted by a chain of between 1 and 4 carbon atoms; tetrabutylammonium hydroxide is preferably used.

The percolated product, represented by the quaternary ammonium salt of the modified polysaccharide, is then freeze-dried.

Preparation of a Partially 2-N-sulphated Derivative
Method A

The quaternary ammonium salt, preferably of tetrabutylammonium, of the partially N-deacetylated polysaccharide, is solubilized in an apolar solvent such as dimethyl sulphoxide, dimethyl formamide, dimethyl acetamide, N-methyl-pyrrolidone, preferably dimethyl formamide (DMFA), at a concentration of between 5 and 50 mg/ml (preferably 25 mg/ml).

The organic solution is supplemented with another solution obtained by solubilizing the sulphating complex constituted by dimethylformamide sulphotrioxide (DMFA-$SO_3$), in DMFA, at a concentration varying between 50 and 200 mg/ml and preferably 100 mg/ml. The quantity of complex to be used, expressed in moles of $SO_3$, proves surprisingly to be equivalent to the moles of amino groups released by the N-deacetylation reaction.

The sulphation reaction proceeds at a temperature of between 0° and 20° C., preferably 4° C. for no longer than 4 hours and is then stopped by adding cold, distilled water.

The reaction solvent is first purified by precipitating the partially 2-N-sulphated hyaluronic acid with ethanol and then dialysing the resolubilized product with distilled water.

Lastly, the solution is freeze-dried and the solid product thus obtained undergoes chemical-analytical characterization to determine the degree of N-sulphation and the mean molecular weight (Table 2).

TABLE 2

| Test | % deacetylation | % N-sulphation | mean MW (Da) |
|---|---|---|---|
| HA | 0 | 0 | 165,000 |
| HA-N-S1 | 5.0 (DAc 2) | 4.8 | 157,000 |
| HA-N-S2 | 14.2 (DAc 4) | 13.9 | 147,000 |
| HA-N-S3 | 23.5 (DAc 5) | 23.0 | 139,000 |
| HA-N-S4 | 36.1 (DAc 6) | 34.2 | 124,000 |

HA = hyaluronic acid
HA-N-S = N-sulphated hyaluronic acid

Preparation of a Partially 2-N-sulphated, 6-O-sulphated Derivative
Method B

The quaternary ammonium salt, preferably of tetrabutylammonium, of the partially N-deacetylated polysaccharide is solubilized in an apolar solvent such as dimethylsulphoxide, demethylformamide, dimethylacetamide, N-methyl-pyrrolidone, preferably dimethylformamide (DMFA), at a concentration of between 5 and 50 mg/ml, preferably 30 mg/ml.

The organic solution is supplemented with another solution obtained by solubilizing the sulphating complex constituted by dimethylformamide sulphotrioxide (DMFA-$SO_3$), in DMFA, at concentrations varying between 50 and 200 mg/ml and preferably 100 mg/ml. The quantity of complex used, expressed as moles of $SO_3$, prove surprisingly to be equivalent to the moles of amino groups released by the N-deacetylation reaction.

The sulphation reaction proceeds at a temperature of between 0° and 20° C., preferably at 4° C. for 4 hours. A solution prepared by solubilizing the pyridine-sulphotrioxide complex in dimethylsulphoxide in such a quantity that the ratio between the moles of $SO_3$ of the sulphating agent and the moles of —$CH_2OH$ comes between 1.1 and 1.3. Larger quantities of reagent may favor any substitution reactions in other alcohol groups (secondary) of the polysaccharide chain.

The reaction then proceeds for another 16 hours at least after which it is stopped by adding cold, distilled water.

All subsequent steps concerning the purification of the modified polysaccharide are those described in "method A".

The analytical characterization performed on the derivatives obtained confirmed that the sulphation method proves surprisingly not only to substitute all the amino groups obtained by the partial N-deacetylation, but also results in the complete substitution of the primary alcohol group of the glucosamine residue of hyaluronic acid (Table 3).

TABLE 3

| Test | % N-deacetylation | % N-sulphation | % 6-O-sulphation |
|---|---|---|---|
| HA-N-O-S1 | 5.0 (DAc 2) | 4.8 | 100 |
| HA-N-O-S1 | 14.2 (DAc 4) | 13.9 | 99.2 |

TABLE 3-continued

| Test | % N-deacetylation | % N-sulphation | % 6-O-sulphation |
|---|---|---|---|
| HA-N-O-S1 | 23.5 DAc 5) | 23.0 | 98.9 |
| HA-N-O-S1 | 36.1 (DAc 6) | 34.2 | 96.5 |

HA-N-O-S1 = hyaluronic acid, N-sulphated and totally O-sulphated in position 6

Moreover, by varying the molar quantities of the pyridine-$SO_3$ complex according to the primary hydroxyl groups (molar ratio of between 0.1 and 1), "method B" enables a series of partially 2-N-sulphated and partially 6-O-sulphated derivatives to be obtained.

Biological Activity

The compounds prepared as described previously are characterized from a biological point of view in such a way as to determine their anticoagulant activity. As reference products, we used the sulphated derivatives of hyaluronic acid obtained according to the method described in international patent application No. WP 95/25751, where the primary and secondary hydroxy groups of the polymer chain are substituted with —$SO_3$— groups according to the quantity of sulphating agent that is used. Moreover, unfractionated heparin (UF heparin) is used as a further reference product, the efficacy of which as an anticoagulant drug has been widely acknowledged for many decades.

Subsequently, the thrombin time (TT test) and whole blood coagulation time (WBCT) were assessed for the following compounds:

| Compound | Description |
|---|---|
| HA 200kDa | hyaluronic acid, sodium salt |
| UF Heparin | unfractionated heparin with mean MW = 15 kDa |
| HA-NS | partially (25%) 2-N-sulphated hyaluronic acid |
| HA-NS-OS | partially 2-N.sulphated (24%) and 6-O-sulphated hyaluronic acid |
| HA-OS | 6-O-sulphated hyaluronic acid |
| HA-2S | hyaluronic acid sulphated with grade 2 substitution |
| HA-3S | hyaluronic acid sulphated with grade 3 substitution |
| HA-4S | hyaluronic acid sulphated with grade 4 substitution |

The ability of the N-sulphated derivatives to prolong blood coagulation time is measured by the thrombin time test performed with a coagulometer. The time it takes to transform fibrinogen into fibrin after the addition of thrombin to a blood sample is determined in the presence of the polymer used as starting material. The test loses its significance when the time exceeds 120 seconds. The coagulation time is determined by simply observing the time it takes for a sample of human blood to coagulate in the presence of the test material. Any times exceeding two hours are not considered.

The results of the tests are reported in Table 4 hereafter:

TABLE 4

| Compound | WBCT (sec) | TT (sec) | UF heparin equivalents[a] |
|---|---|---|---|
| Control | 25 | 10 | — |
| HA 200 kDa | 45 | 11 | — |
| HA-NS | >120 | >120 | 0.46 |
| HA-NS-OS | >120 | >120 | 0.46 |
| HA-OS | 40 | 1 | — |
| HA-2S | 45 | 12.5 | — |

TABLE 4-continued

| Compound | WBCT (sec) | TT (sec) | UF heparin equivalents[a] |
|---|---|---|---|
| HA-3S | >120 | 38 | 0.013 |
| HA-4S | >120 | >120 | 0.46 |

[a]mg of UF heparin necessary to obtain the same effect on coagulation time

Surprisingly, it seems clear that the chemical modification involving the amino group of the glucosamine residue of the polysaccharide chain induces a notable effect on the coagulation time. An identical result can only be obtained by drastically modifying the chemical structure of HA, that is, by substituting all the hydroxyls available per monomeric unit (four) with as many sulphonic groups.

The data obtained show that a degree of sulphation of 0.25, deriving from the previous N-deacetylation and subsequent N-sulphation, is sufficient to act specifically with the factors involving the terminal part of the coagulation cascade, thereby inhibiting the process of transformation of the fibrinogen into fibrin (anticoagulant activity). The presence of the sulphur group in position 6-O of the glucosamine residue does not seem to be a determining factor in the performance of this activity. However, in association with 2-N-sulphated groups, it may play a fundamental role in the inhibition of the Xa factor by interaction with ATIII (antithrombotic activity) and in the inhibition of the factor VIIIa (or vWf) in regulating platelet activation and proliferation.

Analytical Characterization

The chemical-analytical profiles of all the derivatives prepared and described in the present invention have been characterized. The following analytical methodologies were used:

Degree of sulphation (% of sulphur): after undergoing complete combustion in an oxygen-rich environment, the product was analyzed by HPLC using an ionic chromatography technique.

Percentage of 2-N-sulphation: this parameter is indirectly determined by measuring the total sulphonic groups present both before and after N-desulphation of the product, using the method described by Nagasawa (Carbohy. Res. 1977, 58, pages 47–55). The difference between the two values represents the quantity of $SO_3$— groups linked to the amino group of glucosamine.

Percentage of N-deacetylation: this parameter is determined by the method described by J. Riesenfeld (Analy. Bioch. 1990, vol. 188, pages 383–389).

Mean molecular weight: this parameter is determined by GPC, using a set of Shadex and B-803 and B-806 columns, a multi-angle-laserlight-scattering monitor (MALLS) and a refractometer to measure the index of refraction (RI).

EXAMPLES

Example 1

Preparation of Partially 2-N-sulphated Hyaluronic Acid (Wherein about 5% of the N-acetyl Groups are Substituted by Sulphated Groups)

1.00 gr of HA from rooster combs, with a mean molecular weight of 181,000 Da, is solubilized in 50 ml of hydrazine monohydrate together with 0.5 gr of hydrazine sulphate.

The solution is maintained under agitation while the reaction is continued for 8 hours at 60° C., after which it is stopped by the addition of 100 ml of ethanol. The gelatinous precipitate thus formed is washed with ethanol and then dried at room temperature under reduced pressure.

The intermediate product is solubilized in a mixture constituted by 50 ml of water and 20 ml of a 10% solution of sodium acetate, and is treated lastly with 25 ml of a solution of iodic acid at a concentration of 0.5M. After about 30 minutes' reaction under agitation, the excess iodine is titrated with 5 ml of a 57% solution of iodohydric acid. During this operation it is preferable to keep the reaction container cold with ice. The rich brown solution is then treated at least five times with 30 ml aliquots of diethyl ether to extract the reaction residues from the aqueous solution containing the modified polymer. It is finally concentrated, at reduced pressure and at a temperature of 40° C., to a volume of about 40 ml and then percolated through a column filled with 20 ml of ion exchange sulphonic resin activated with a 40% solution w/v of tetrabutylammonium hydroxide.

The aqueous solution containing the modified polysaccharide in the form of tetrabutylammonium salt (HATBA) is then harvested and subjected to one lyophilization cycle.

1.30 gr of freeze-dried HA salt of TBA is solubilized in 45 ml of dimethylformamide and the solution thus obtained is supplemented with 0.6 ml of a solution of a complex of N-N dimethylformamide sulphotrioxide at a concentration of 50 mg/ml. The reaction continues for 5 hours at 4° C. under continuous, gentle agitation, after which it is stopped by adding 45 ml of cold, distilled water. Having neutralized the solution with NaOH 2 M, bringing it to a pH of between 7.5 and 8, it is then filtered through a Gooch filter with pore size G2 and treated with 250 ml of ethanol.

The precipitate thus formed is washed with at least 150 ml of ethanol and vacuum-dried for at least 16 hours, after which it is resolubilized in 50 ml of distilled water and then dialysed against 50 volumes of water.

The product is freeze-dried and then characterized to determine the percentage of N-substituted amino groups and its mean molecular weight.

| | |
|---|---|
| Weight of the freeze-dried product: | 0.72 gr; yield: 85% |
| moles of $SO_3$/moles of HA (monomeric units) | 0.045 |
| moles of free —$NH_2$ groups/moles of HA: | 0.052 |
| % of de-N-acetylation: | 5.2% |
| % of re-N-sulphation | 4.5% |
| yield from the N-sulphation reaction: | 87% |
| mean molecular weight: | 174,000 Da |

Example 2

Preparation of Partially 2-N-sulphated Hyaluronic Acid (Wherein about 25% of the N-acetyl Groups are Substituted with Sulphated Groups 1.2 gr of HA from rooster combs, with a mean molecular weight of 181,000 Da, is solubilized in 60 ml of hydrazine monohydrate together with 0.6 gr of hydrazine sulphate.

The solution is maintained under agitation while the reaction proceeds for 24 hours at 60° C., after which it is stopped by the addition of 120 ml of ethanol. The gelatinous precipitate thus formed is washed with ethanol and then dried at room temperature under reduced pressure.

The intermediate product is solubilized in a mixture constituted by 60 ml of water and 25 ml of a 10% solution of sodium acetate, and is treated lastly with 30 ml of a solution of iodic acid at a concentration of 0.5M. After about 30 minutes' reaction under continuous agitation, the excess iodine is titrated with 6 ml of a 57% solution of iodohydric acid. During this operation it is preferable to keep the reaction container cold with ice.

The rich brown solution is then treated at least five times with 40 ml aliquots of diethyl ether to extract the reaction residues from the aqueous solution containing the modified polymer. It is finally concentrated, at reduced pressure and at a temperature of 40° C., to a volume of about 50 ml and then percolated through an ion exchange column filled with 25 ml of sulphonic resin activated with a 40% solution w/v of tetrabutylammonium hydroxide.

The aqueous solution containing the modified polysaccharide in the form of tetrabutylammonium salt (HATBA) is then harvested and subjected to one lyophilization cycle.

1.65 gr of freeze-dried HA salt of TBA is solubilized in 55 ml of dimethylformamide and the solution thus obtained is supplemented with 3.0 ml of solution at a concentration of 50 mg/ml of a complex of N-N dimethylformamide sulphotrioxide. The reaction continues for 6 hours at 4° C. under continuous, gentle agitation, after which it is stopped by adding 55 ml of cold, distilled water. Having neutralized the solution with NaOH 2 M, bringing it to a pH of between 7.5 and 8, it is then filtered through a Gooch filter with pore size G2 and treated with 300 ml of ethanol.

The precipitate thus formed is washed with at least 150 ml of ethanol and vacuum-dried for at least 16 hours, after which it is resolubilized in 50 ml of distilled water and then dialysed against 50 volumes of water.

The product is freeze-dried and then characterized to determine the percentage of N-substituted amino groups and its mean molecular weight.

| | |
|---|---|
| Weight of the freeze-dried product: | 0.98 gr; yield: 89% |
| moles of $SO_3$/moles of HA (monomeric units) | 0.23 |
| moles of free —$NH_2$ groups/moles of HA: | 0.24 |
| % of de-N-acetylation: | 24% |
| % of re-N-sulphation: | 23% |
| yield from the N-sulphation reaction: | 96% |
| mean molecular weight: | 161,000 Da |

Example 3

Preparation of Hyaluronic Acid, Partially 2-N-sulphated (Wherein about 25% of the N-acetyl Groups are Substituted by Sulphated Groups) and 6-O-sulphated 5.0 gr of HA obtained by fermentation, with a mean molecular weight of 195,000 Da, is solubilized in 250 ml of hydrazine monohydrate together with 2.5 gr of hydrazine sulphate.

The reaction is maintained under agitation for 24 hours at 60° C., after which it is stopped by the addition of 500 ml of ethanol. The gelatinous precipitate thus formed is washed with ethanol and then dried at room temperature under reduced pressure.

The intermediate product is solubilized in a mixture constituted by 250 ml of water and 105 ml of a 10% solution of sodium acetate, and is treated lastly with 125 ml of a solution of iodic acid at a concentration of 0.5M. After about 30 minutes' reaction under continuous agitation, the excess iodine is titrated with 25 ml of a 57% solution of iodohydric acid. During this operation it is preferable to keep the reaction container cold with ice.

The rich brown solution is then treated at least five times with 150 aliquots of diethyl ether to extract the reaction residues from the aqueous solution containing the modified polymer. It is finally concentrated, at reduced pressure and at a temperature of 40° C., to a volume of about 200 ml and then percolated through a column filled with 100 ml of ion exchange sulphonic resin activated with a 40% solution w/v of tetrabutylammonium hydroxide.

The aqueous solution containing the modified polysaccharide in the form of tetrabutylammonium salt (HATBA) is then harvested and subjected to one lyophilization cycle.

6.0 gr of freeze-dried HA salt of TBA is solubilized in 300 ml of dimethylformamide and the solution thus obtained is supplemented with 13 ml of a solution of a complex of N-N dimethylformamide sulphotrioxide at a concentration of 50 mg/ml. The reaction continues for 6 hours at 4° C. under continuous, gentle agitation.

A second solution, constituted by 40 ml of a complex of pyridine sulphotrioxide solubilized in dimethyl sulphoxide at a concentration of 50 mg/ml is added to the reaction mixture.

Approximately sixteen hours later, 250 ml of cold, distilled water is added and, once the solution has been neutralized with NaOH 2 M to a pH of 8, it is then filtered through a Gooch filter with pore size G3 and treated with 1,250 ml of ethanol.

The precipitate thus formed is washed with at least 500 ml of ethanol and vacuum-dried for at least 16 hours, after which it is resolubilized in 250 ml of distilled water and then dialysed against 50 volumes of water.

The product is freeze-dried and then characterized to determine the percentage of N-substituted amino groups, the degree of 6-O-sulphation and its mean molecular weight.

| | |
|---|---|
| Weight of the freeze-dried product: | 4.12 gr; yield: 82% |
| moles of $SO_3$/moles of HA (monomeric units) | 1.24 |
| moles of free —$NH_2$ groups/moles of HA: | 0.26 |
| % of de-N-acetylation: | 26% |
| % of re-N-sulphation: | 24% |
| % of O-sulphation: | 100% |
| mean molecular weight: | 170,000 Da |

Example 4

Preparation of the Benzyl Ester of Hyaluronic Acid, Partially N-sulphated and O-sulphated 2.00 gr of the derivative obtained in Example 3 is solubilized in 100 ml of distilled water and the solution is percolated through a glass column previously filled with 40 ml of ion exchange resin activated with tetrabutylammonium hydroxide (TBA+ form). The eluate is freeze-dried and 3.3 gr of product is obtained.

The product is solubilized in a mixture constituted by 130 ml of N-methyl pyrrolidone and 1.3 ml of water, reacted at 4° C. with 0.29 ml of benzyl bromide. The reaction proceeds for 48 hours at 28° C., keeping the solution under agitation and away from sources of light, after which 300 ml of ethyl acetate is added.

The precipitate thus formed, mainly constituted by the modified polysaccharide, is washed with 100 ml of acetone and then vacuum-dried at room temperature, after which it is treated with 100 ml of a 10% solution w/v of sodium chloride.

At the end of the saline treatment (which lasts about one hour), the product is washed with 150 ml of water/acetone 20:80 and lastly with 100 ml of acetone.

After drying for 48 hours at 30° C., 0.92 gr at a yield of 80% is obtained.

| | |
|---|---|
| Characterization: % of esterification | 96% |

Example 5

Preparation of 10% Autocrosslinked Hyaluronic Aid, Partially N-sulphated and O-sulphated 2.00 gr of the derivative obtained in example 3 are solubilized in 100 ml of distilled water and the solution is percolated through a glass column filled with 40 ml of ion exchange resin activated with tetrabutylammonium hydroxide (TBA+ form). After freeze-drying the eluate, 3.3 gr of product are obtained.

The product is solubilized in a mixture formed by 165 ml of N-methyl pyrrolidone (NMP) and 0.8 ml of water, and then reacted with a solution obtained by solubilizing 205 mg of 2-chloro-1-methyl pyridine iodide in 8.2 ml of NMP. The reaction proceeds for 18 hours at −20° C., after which 165 ml of an aqueous solution of 3% ammonium acetate is added.

The mixture is constantly agitated for about 4 hours and then treated with 650 ml of ethanol. The precipitate thus formed is separated by filtration, washed with ethanol and then vacuum-dried for 24 hours.

The product is then treated with 60 ml of a 3% solution of sodium chloride so as to favor ion exchange and lastly reprecipitated by adding 180 ml of ethanol to the solution. After eliminating the supernatant the product is washed at least three times with 50 ml of ethanol and is then treated with 100 ml of acetone before being finally dried at 30° C. for 48 hours.

0.97 gr of sulphated and partially autocrosslinked derivative are thus obtained.

Example 6

Preparation of a Film of Benzyl Ester of Hyaluronic Acid Partially N-sulphated and O-sulphated A solution of the benzyl ester of hyaluronic acid, partially N-sulphated and O-sulphated is prepared in dimethylsulphoxide at a concentration of 180 mg/ml.

A thin layer of solution is spread over a glass plate; the thickness of the layer of solution must be 10 times greater than that of the final film. The glass plate is immersed in ethanol which absorbs the dimethylsulphoxide without solubilizing the ester, which solidifies. The film is separated from the glass plate and repeatedly washed with ethanol, water and then again with ethanol.

The film obtained is dried under pressure for 48 hours at 30° C.

Example 7

Preparation of the Silver Salt of the Partially 2-N-sulphated (25%) and 6-O-sulphated Hyaluronic Acid Derivative 0.50 gr of compound obtained according to example 2, is solubilized in 25 ml of distilled water and the solution obtained is percolated through a column filled with 16 cm³ of strong ion exchange resin in H+ form. The eluate is then harvested and freeze-dried. The intermediate product in acid form obtained by freeze-drying is treated with 20 ml of a 0.5 M solution of AgNO₃ for 60 minutes under agitation and away from the light.

Having eliminated the liquid phase by filtration, the product is thoroughly washed with 150 ml of distilled water and then with 50 ml of absolute ethanol. After vacuum-drying the sulphated hyaluronic acid derivative, silver salt, at 40° C., 0.649 gr are obtained (yield 95%).

Example 8

Coating of a Cardiac Valve Made of Polyurethane with Partially 2-N-sulphated (25%) and 6-O-sulphated Hyaluronic Acid A cardiac valve made of polyurethane is treated with oxygen plasma produced with a radio frequency generator.

The working conditions are as follows: the pressure in the reaction chamber is set at 100 mtorr, the strength of the plasma generator is 50 W, the oxygen flow is set at 20 cm³/min. and the treatment time is 30 sec.

The device thus treated is then immersed in 250 ml of a 0.65% solution of polyethylene amine with a molecular weight of 500,000, and left to soak there for 90 minutes. After thorough washing with distilled water, the material is placed in contact with 250 ml of an aqueous solution obtained by solubilizing 2.5 gr of partially 2-N-sulphated and 6-O-sulphated derivative, obtained as described in example 2. Moreover, the following substances are added in stoichiometric quantities with regard to the carboxy groups belonging to the modified polysaccharide: 0.76 gr of N-hydroxysuccinimide (NHS) and 1.23 gr of 3-dimethylaminopropyl-1-ethyl carbodiimide (EDC). The reaction proceeds for about 16 hours at room temperature.

Lastly, the device coated with the sulphated hyaluronic acid derivative is thoroughly washed with distilled water and then blown dry.

The invention being thus described, it is clear that these methods can be modified in various ways. Such modifications are not to be considered as divergences from the spirit and purpose of the invention and any such modifications as would appear evident to an expert in the field come within the scope of the following claims.

What is claimed is:

1. A sulphated hyaluronic acid compound, a derivative thereof, or a salt thereof, wherein said sulphated hyaluronic acid compound, derivative, or salt thereof has between 3.0% and 36.1% N-deacetylation and wherein the glucosamines of said compound or said derivative thereof are partially N-sulphated or partially N-sulphated and totally or partially O-sulphated in position 6.

2. The sulphated hyaluronic acid compound according to claim 1, wherein said hyaluronic acid derivative is a total or partial ester with an aliphatic, aromatic, arylaliphatic, cycloaliphatic or heteroaliphatic alcohol.

3. The sulphated hyaluronic acid compound according to claim 2, wherein said hyaluronic acid derivative is selected from the group consisting of:

a total ester of hyaluronic acid with benzyl alcohol, a partial ester of hyaluronic acid wherein about 25% of the carboxy groups of the hyaluronic acid are esterified with benzyl alcohol, a partial ester of hyaluronic acid wherein about 50% of the carboxy groups of the hyaluronic acid are esterified with benzyl alcohol, a partial ester of hyaluronic acid wherein about 75% of the carboxy groups of the hyaluronic acid are esterified with benzyl alcohol, a total ester of hyaluronic acid with ethyl alcohol, a partial ester of hyaluronic acid wherein about 25% of the carboxy groups of the hyaluronic acid are esterified with ethyl alcohol, a partial ester of hyaluronic acid wherein about 50% of the carboxy groups of the hyaluronic acid are esterified with ethyl alcohol, a partial ester of hyaluronic acid wherein about 75% of the carboxy groups of the hyaluronic acid are esterified with ethyl alcohol, an ester of hyaluronic acid wherein the carboxy groups of the hyaluronic acid are esterified with dodecyl alcohol to an extent of between 5% and 100%, and an ester of hyaluronic acid wherein the carboxy groups of the hyaluronic acid are esterified with hexadecyl alcohol to an extent of between 5% and 100%.

4. The sulphated hyaluronic acid compound according to claim 1, wherein said hyaluronic acid derivative is a crosslinked compound, wherein a part or all the carboxy groups of the D-glucuronic residue form inner esters or inter-molecular esters with the alcohol functions of the same polysaccharide chain or other chains respectively.

5. The sulphated hyaluronic acid compound according to claim 1, wherein the hyaluronic acid derivative is a crosslinked compound, wherein said crosslinked compound is formed by reacting a part or all of the carboxy groups of the D-glucuronic residue with polyalcohols of an aliphatic, aromatic, arylaliphatic, cycloaliphatic or heterocyclic series, to thereby generate crosslinking by means of spacer chains.

6. The sulphated hyaluronic acid compound according to claim 1, wherein said compound or said derivative thereof is salified with a heavy metal.

7. The sulphated hyaluronic acid compound according to claim 6, wherein the heavy metal is a metal element selected from the 4th, 5th and 6th groups of the periodic table of elements.

8. The sulphated hyaluronic acid compound according to claim 7, wherein said heavy metal is silver, cobalt, iron, copper, zinc, arsenic, strontium, zirconium, antimony, gold, cesium, tungsten, selenium, platinum, ruthenium, bismuth, tin, titanium, or mercury.

9. The sulphated hyaluronic acid compound according to claim 1, wherein said compound or said derivative thereof that is salified with a pharmacologically active substance.

10. The sulphated hyaluronic acid compound according to claim 9, wherein the pharmacologically active substance is selected from the group consisting of an antibiotic, an antiinfective, an antimicrobial, an antiviral, a cytostatic, an antitumoral, an antiinflammatory, a wound healing agent, an anaesthetic, a cholinergic agonist, a cholinergic antagonist, an adrenergic agonist, an adrenergic antagonist, an antithrombotic, an anticoagulant, a haemostatic, a fibrinolytic, a thrombolytic agent, a protein, a protein fragment, a peptide, and a polynucleotide.

11. The sulphated hyaluronic acid compound according to claim 1, wherein the degree of sulphation per dimeric unit of the amino groups varies between 1 and 70% and that of the hydroxyl group in position 6 varies between 0 and 100%.

12. The sulphated hyaluronic acid compound according to claim 1, wherein the degree of sulphation per dimeric unit of the amino groups varies between 5 and 40% and that of the hydroxyl group in position 6 varies between 0 and 100%.

13. A pharmaceutical composition containing therein a pharmaceutically effective amount of a sulphated hyaluronic acid compound or a derivative thereof, wherein said sulphated hyaluronic acid compound, derivative thereof has between 3.0–36.1% N-deacetylation and wherein the glucosamines of said compound or said derivative thereof are partially N-sulphated or partially N-sulfated and totally or partially O-sulphated in position 6, said compound or said derivative optionally being salified and optionally being in association with another pharmacologically active substance, and a pharmaceutically acceptable carrier therefor.

14. The pharmaceutical composition according to claim 13, wherein said hyaluronic acid derivative is a total or partial, ester with an aliphatic, aromatic, arylaliphatic, cycloaliphatic or heteroaliphatic alcohol.

15. The pharmaceutical composition according to claim 14, wherein said hyaluronic acid derivative is selected from the group consisting of:
- a total ester of hyaluronic acid with benzyl alcohol,
- a partial ester of hyaluronic acid wherein about 25% of the carboxy groups of the hyaluronic acid are esterified with benzyl alcohol,
- a partial ester of hyaluronic acid wherein about 50% of the carboxy groups of the hyaluronic acid are esterified with benzyl alcohol,
- a partial ester of hyaluronic acid wherein about 75% of the carboxy groups of the hyaluronic acid are esterified with benzyl alcohol,
- a total ester of hyaluronic acid with ethyl alcohol, a partial ester of hyaluronic acid wherein about 25% of the carboxy groups of the hyaluronic acid are esterified with ethyl alcohol, a partial ester of hyaluronic acid wherein about 500 of the carboxy groups of the hyaluronic acid are esterified with ethyl alcohol,
- a partial ester of hyaluronic acid wherein about 75% of the carboxy groups of the hyaluronic acid are esterified with ethyl alcohol,
- an ester of hyaluronic acid wherein the carboxy groups of the hyaluronic acid are esterified with dodecyl alcohol to an extent of between 5% and 100%, and
- an ester of hyaluronic acid wherein the carboxy groups of the hyaluronic acid are esterified with hexadecyl alcohol to an extent of between 5% and 100%.

16. The pharmaceutical composition according to claim 13, wherein said hyaluronic acid derivative is a crosslinked compound, wherein a part or all the carboxy groups of the D-glucuronic residue form inner esters or inter-molecular esters with the alcohol functions of the same polysaccharide chain or other chains respectively.

17. The pharmaceutical composition according to claim 13, wherein the hyaluronic acid derivative is a crosslinked compound, wherein said crosslinked compound is formed by reacting a part or all of the carboxy groups of the D-glucuronic residue with polyalcohols of an aliphatic, aromatic, arylaliphatic, cycloaliphatic or heterocyclic series, to thereby generate crosslinking by means of spacer chains.

18. The pharmaceutical composition according to claim 13, wherein said compound or said derivative thereof is salified with a heavy metal.

19. The pharmaceutical composition according to claim 13, wherein the heavy metal is a metal element selected from the 4th, 5th and 6th groups of the periodic table of elements.

20. The pharmaceutical composition according to claim 13, wherein said heavy metal is silver, cobalt, iron, copper, zinc, arsenic, strontium, zirconium, antimony, gold, cesium, tungsten, selenium, platinum, ruthenium, bismuth, tin, titanium, or mercury.

21. The pharmaceutical composition according to claim 13, wherein said compound or said derivative thereof that is salified with a pharmacologically active substance.

22. The pharmaceutical composition according to claim 13, wherein the pharmacologically active substance is selected from the group consisting of an antibiotic, an antiinfective, an antimicrobial, an antiviral, a cytostatic, an antitumoral, an antiinflammatory, a wound healing agent, an anaesthetic, a cholinergic agonist, a cholinergic antagonist, an adrenergic agonist, an adrenergic antagonist, an antithrombotic, an anticoagulant, a haemostatic, a fibrinolytic, a thrombolytic agent, a protein, a protein fragment, a peptide, a polynucleotide, growth factors, enzymes, vaccines, and substances used in the treatment of diseases associated with genetic defects, deforming disorders and hereditary diseases.

23. The pharmaceutical composition according to claim 13, wherein the degree of sulphation per dimeric unit of the amino groups varies between 1 and 70% and that of the hydroxyl group in position 6 varies between 0 and 100%.

24. The pharmaceutical composition according to claim 13, wherein the degree of sulphation per dimeric unit of the amino groups varies between 5 and 40%, and that of the hydroxyl group in position 6 varies between 0 and 100%.

25. A sulphated hyaluronic acid compound, a derivative thereof, or a salt thereof according to claim 1, alone or in association with one another and/or with a pharmacologically active substance for the preparation of pharmaceutical compositions.

26. The sulphated compound according to claim 25, wherein the pharmacologically active substance is selected from, the group consisting of antibiotics, anti-infective, antimicrobial, antiviral, cytostatic, antitumoral, anti-inflammatory and wound healing agents, anaesthetics, cholinergic or adrenergic agonists and antagonists, antithrombotic, anticoagulant, haemostatic, fibrinolytic, thrombolytic agents, proteins and their fragments, peptides, polynucleotides, growth factors, enzymes, vaccines, substances used in the treatment of diseases associated with genetic defects, deforming disorders and hereditary diseases.

* * * * *